United States Patent [19]
Shih et al.

[11] Patent Number: 5,627,159
[45] Date of Patent: May 6, 1997

[54] ENHANCEMENT OF LIPID CATIONIC TRANSFECTIONS IN THE PRESENCE OF SERUM

[75] Inventors: PoJen Shih, Columbia; Pamela Hawley-Nelson, Silver Spring; Joel A. Jessee, Mt. Airy, all of Md.

[73] Assignee: Life Technologies, Inc., Gaithersburg, Md.

[21] Appl. No.: 329,969

[22] Filed: Oct. 27, 1994

[51] Int. Cl.$^6$ ............... A61K 48/00; A61K 9/127; C12N 5/00
[52] U.S. Cl. ............. 514/44; 424/450; 435/172.1; 435/172.3; 935/52; 935/54
[58] Field of Search ............... 435/240.1, 240.2, 435/172.1; 424/450; 514/44; 935/52, 54

[56] References Cited

PUBLICATIONS

Brunette et al (1992) Nucleic Acids Research 20:1151.
Zhou et al (1991) Biochimica et BioPhysica Acta 1065:8–14.

*Primary Examiner*—Bruce R. Campbell
*Attorney, Agent, or Firm*—Greenlee, Winner & Sullivan, P.C.

[57] ABSTRACT

A method is provided for enhancing transfection efficiency of eukaryotic cells comprising contacting said cells with a lipid aggregate comprising nucleic acid and a polycationic lipid composition in the presence of a polycationic compound and serum. The polycationic compound is preferably Polybrene™, and the lipid aggregate preferably comprises liposomes of nucleic acid and LipofectAMINE™.

11 Claims, 2 Drawing Sheets

ENHANCEMENT OF LIPID CATIONIC TRANSFECTIONS IN THE PRESENCE OF SERUM

FIELD OF THE INVENTION

This invention is in the field of genetic engineering, in particular methods for enhancing the efficiency of transformation of eukaryotic cells.

BACKGROUND OF THE INVENTION

Cationic lipid reagents are the most effective and simplest method for DNA transfection of eukaryotic cells. A number of such reagents are known to the art, e.g. as described in U.S. patent applications 08/090,290, abandoned, 08/195, 866, 08/171,232. Lipofectin™ (Gibco/BRL:Life Technologies, Inc., Gaithersburg, Md.; Felgner, P. L., et al. (1987) Proc. Natl. Acad. Sci. USA 84:7413) and LipofectACE™ (Whitt, M. A., et al. (1991) Focus 13:8) reagents contain monocationic lipids and are highly effective at transfection in the presence or absence of serum (Brunette, E., et al. (1992) Nuc. Acids Res. 20:1151; Ciccarone, V., et al. (1993) Focus 15, 80.). LipofectAMINE™ reagent (U.S. Pat. No. 5,334,761; Gibco/BRL:Life Technologies, Inc., Gaithersburg, Md.) contains a polycationic lipid and is up to 30-fold more active in serum-free transfection than the monocationic reagents (Hawley-Nelson, P., et al. (1993) Focus 15:73). However LipofectAMINE™ transfection activity is decreased in the presence of serum and is roughly equal to that of the monocationic reagents.

U.S. Pat. No. 5,286,634 of Stadler et al. for "Synergistic Method for Host Cell Transformation" issued Feb. 15, 1994 discloses the use of a polycationic compound to treat a host cell for a period of time prior to treating with a DNA-liposome complex to improve transformation of the cell. The invention was exemplified using plant cells which do not require serum in culture media or in vivo. The method of said patent is not believed effective in enhancing transfection of mammalian cells because the preferred polycationic compound of said patent (Polybrene™), is toxic to mammalian cells in the absence of serum.

A problem with transfection of eukaryotic cells by means of liposomes is the fact that culturing such cells in vitro requires the use of serum in the medium for best results, and the use of serum in culture media is standard in the art. However, the use of serum in the culture medium substantially inhibits the efficiency of liposome transfection. Further, in the transfection of animal cells in vivo, serum is inherently present, again with an inhibiting effect on the efficiency of liposome transfection. Therefore a need exists for a method of eukaryotic transfection in the presence of serum which counteracts the inhibiting effects of the serum.

In addition, some liposomes are toxic to the cells being transformed. Thus, a method for counteracting the toxic effects of liposomes is needed to improve the efficiency of liposome transfection of eukaryotic cells.

All publications and patents referred to herein are specifically incorporated by reference in their entirety.

SUMMARY OF THE INVENTION

Figure 1:
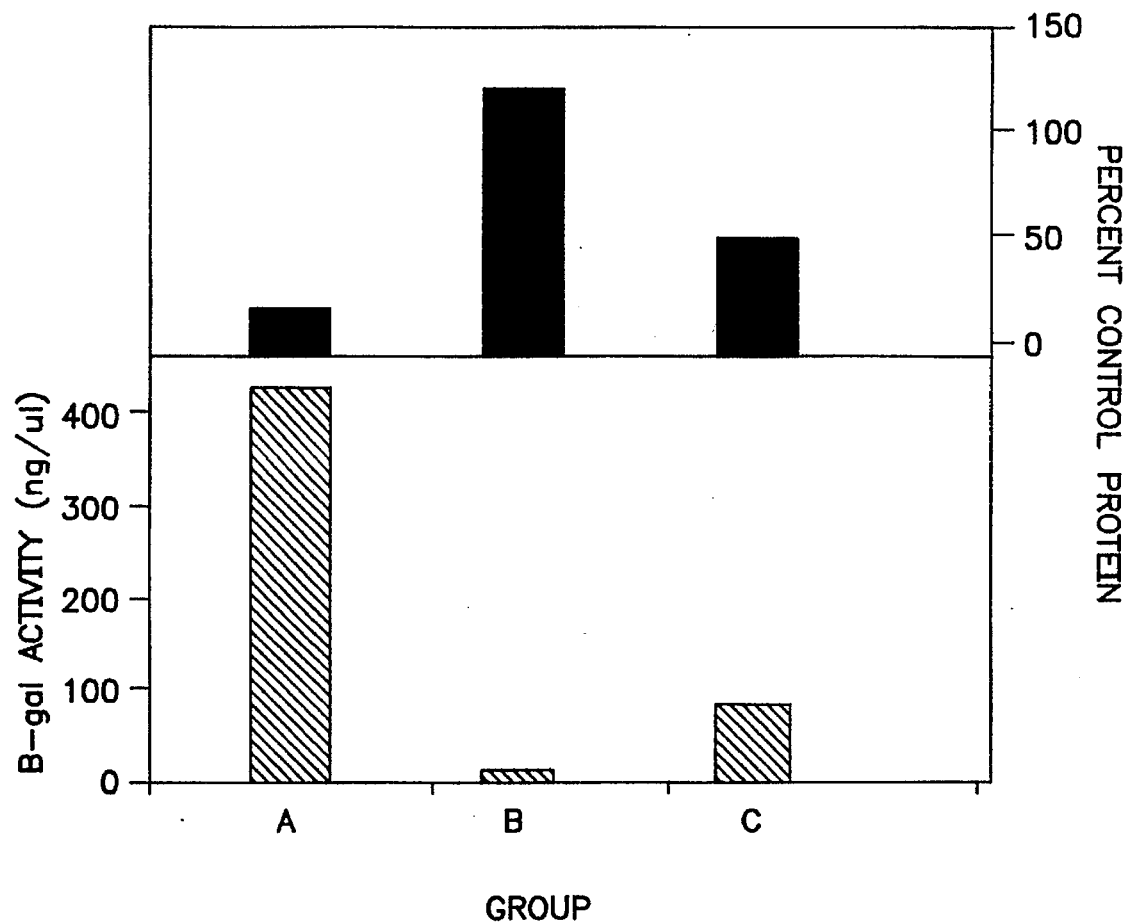
FIG. 1 is a bar graph showing Polybrene™ enhancement of β-gal activity in transfections of BHK-21 cells in serum and inhibition of protein levels in the presence of serum. Group A are cells transfected using 6 μl LipofectAMINE™, no Polybrene™ and no fetal bovine serum (FBS); Group B are cells transfected using 6 μl LipofectAMINE™, and no Polybrene™, with 5% fetal bovine serum present; Group C are cells transfected using 18 μl LipofectAMINE™, and 20 μl Polybrene™, with 5% fetal bovine serum present.

A method is provided for enhancing transfection efficiency of eukaryotic cells comprising contacting said cells with a lipid aggregate comprising nucleic acid and a cationic lipid in the presence of a polycationic compound and serum. The polycationic compound is preferably Polybrene™.

The polycationic compound is present at a concentration of about 20 to about 80 μg/ml, more preferably between about 20 and about 40 μg/ml. The lipid aggregate, which is composed of liposomes of nucleic acid and cationic lipid, preferably comprises between about 5 and about 20 μl per ml, more preferably between about 12 and about 15 μl per ml.

Some lipid aggregates are toxic to cells, and the use of the polycationic in the method of this invention substantially decreases such toxicity as measured in vitro by proteins present in the medium as a result of cell lysis, or as measured by means known to the art.

The method of this invention is applicable to eukaryotic cells, preferably mammalian, and more preferably human cells, and may be performed in vivo, e.g. in gene therapy as known to the art, or in vitro in cell culture, also as known to the art.

In the preferred embodiment of this invention, the polycationic compound is Polybrene™ and the lipid aggregate comprises cationic liposomes of LipofectAMINE™ and DNA.

Transfection efficiency is "enhanced" when an improvement of at least about 5 percent, preferably about 10 percent, and more preferably about 20 percent in efficiency is shown using the protocols set forth in the examples hereof.

"Lipid Aggregate" is a generic term which includes liposomes of all types, both unilamellar and multilamellar, as well as micelles and more amorphous aggregates of cationic lipid or lipid mixed with amphipathic lipids such as phospholipids.

"Target Cell" refers to any cell to which a desired compound is delivered, using a lipid aggregate as carrier for the desired compound.

"Transfection" is used herein to mean the delivery of expressible nucleic acid to a target cell, such that the target cell is rendered capable of expressing said nucleic acid. It will be understood that the term "nucleic acid" includes both DNA and RNA without regard to molecular weight, and the term "expression" means any manifestation of the functional presence of the nucleic acid within the cell, including without limitation, both transient expression and stable expression. Transfection may be performed in vitro or in vivo, and in this invention is performed in the presence of serum.

"Delivery" is used to denote a process by which a desired compound is transferred to a target cell such that the desired compound is ultimately located inside the target cell, or in or on the target cell membrane.

"Polycationic compound" include hexadimethrine bromide (Polybrene™) or other salts of hexadimethrine as a preferred species. This term also includes compounds such as the salts of poly-L-ornithine, poly-L-arginine, poly-L-lysine, poly-D-lysine, polyalylamine and polyethyleneimine. In addition, any polycationic compound prepared from the combination of any compound containing at least two good leaving groups, such as dihalogenated compounds especially dibromide and diiodide, but less desirably difluoride, or ditosylates and any poly(tetraalkyl-substituted amine) containing chains of two or more carbons between the amine groups could also serve as an effective polycationic compound of this invention. In the instance of the salt of hexadimethrine, the compound containing two good leaving groups could be 1,3 dibromopropane and the poly(tetraalky) substituted amine is N,N,N',N'-tetramethylhexamethylene diamine. In this case the polyamine is a diamine. Indeed, almost any combination of alkyl or xylyl groups attached to a basic carbon chain and combined using the aforementioned good leaving groups would be effective polycations. However, for reasons regarding weakening the basicity of the compound, it is believed that aryl groups attached directly to nitrogen compounds would be less effective than the foregoing compounds.

The cationic liposomes of this invention are prepared by methods well known in the art (e.g. Felgner, P. L., et al. (1987), Proc. Natl. Acad. Sci. USA 4:7413–7417), or are available commercially. Lipofectin™, LipofectACE™ and LipofectAMINE™ of Gibco/BRL:Life Technologies, Inc., Gaithersburg, Md.) are preferred cationic liposomes with LipofectAMINE™ being most preferred.

Eukaryotic cells, as known to the art, are cells with visibly evident nuclei, such as plant and animal cells, more preferably animal cells including insect cells, and mammalian cells, more preferably human cells and higher mammalian cells.

Serum, as is known to the art, is the watery portion of an animal fluid remaining after coagulation. Preferably the serum used herein is mammalian blood serum, more preferably sera commercially available for use in the culturing of mammalian cells, and most preferably is fetal bovine serum (FBS).

The cells being transfected may be contacted with the polycationic compound of this invention by first treating the cells with said compound to form a complex with said cells prior to contacting with the lipid aggregate comprising nucleic acid, or by mixing the polycationic compound with the lipid aggregate comprising nucleic acid prior to contacting the cells with this mixture.

A lipid aggregate or cationic liposome of this invention may be toxic to the cells being transfected. Toxicity is determined by cell death which may be measured by protein in the medium caused by cell lysis.

DETAILED DESCRIPTION OF THE PREFERRED EMBODIMENTS

Applicants have shown that addition of the polycation Polybrene™ (Sigma Chemical Co., St. Louis, Mo.), hexadimethrine bromide to serum-containing medium used in LipofectAMINE™-mediated transfections allows up to 30-fold higher transfection in BHK21 and COS7 cells compared to the activity seen in the presence of serum.

A panel of polycationic compounds was screened in LipofectAMINE™ transfections in the presence of serum, and Polybrene™ was selected as a preferred polycationic compound of this invention since it showed higher trans-fection frequency and lower cell toxicity (data not shown). Additionally, Polybrene™ is an FDA-approved reagent for gene therapy.

The continued presence of serum during transfections has advantages in several circumstances. Loss of cells during the transfection is diminished, and stimulation of gene expression by the altered levels of serum hormones can be avoided. Previous reports of serum inhibition of cationic lipid-mediated transfections (Felgner, P. L. and Ringold, G. M. (1989) Nature 337, 387) have suggested that the inhibition was due to the presence of sulphated proteoglycans in the serum. Transfections with monocationic lipid reagents are not inhibited by serum when DNA-lipid complexes are made in serum-free conditions (Brunette, E., et al. (1992) Nuc. Acids Res. 20:1151; Ciccarone, V., et al. (1993) Focus 15, 80). The inhibition of LipofectAMINE™ transfections by serum occurs even when complexes are made in serum-free conditions (Ciccarone, V., et al. (1993) Focus 15, 80; Hawley-Nelson, P., et al. (1993) Focus 15:73). This inhibition now can be overcome by addition of optimal concentration polycationic compounds such as the polycationic reagent Polybrene™.

Polybrene™ is toxic to cells in the absence of serum, and toxicity is greatly decreased in the presence of serum. Any residual toxicity remaining in the presence of serum may be reduced by adjustment of Polybrene™ and serum dosage.

EXAMPLES

Example 1

BHK21 and COS7 cells were cultured in DMEM (GIBCO BRL) with 10% fetal bovine serum (GIBCO BRL), 100 units/ml penicillin and 100 µg/ml streptomycin, and passaged the day before transfection to 6-well or 24-well plates. For transfection, LipofectAMINE™ Reagent (GIBCO BRL) and plasmid pCMVβgal (MacGregor, G. R., and Caskey, C. T. (1989) Nuc. Acids Res. 17, 2365) DNA were diluted separately into OPTIMEM I™ Reduced Serum Medium (GIBCO BRL) without serum. The lipid and DNA solutions were combined, gently mixed, and incubated at room temperature for 15–45 min to form DNA-lipid complexes. The cells were rinsed with DMEM, and transfection medium consisting of DMEM with or without 5% FBS and variable concentrations of Polybrene™ (SIGMA). The DNA-lipid complexes were added to the transfection medium on the cells and gently mixed. The transfection medium was replaced with complete growth medium after a 5 hour exposure. ONPG enzyme assays (Sambrook et al. (1989) Molecular Cloning: A Laboratory Manual, Cold Spring Harbor Laboratory Press, Cold Spring Harbor, New York) and X-gal in situ staining (Sanes, J. R., et al. (1986) EMBO J. 5, 3133) were performed 24 to 30 hr after transfection.

$1 \times 10^5$ BHK-21 cells were plated per 35 mm well (6-well plate). The day after plating, cells were rinsed with DMEM and fed 0.8 ml of DMEM with or without polybrene™ and 5% FBS. The cells were transfected with 1 µg pCMV βgal DNA and LipofectAMINE™ Reagent. The day after transfection, cells were rinsed with PBS, fixed and stained with X-gal. Peak activity points from the dose-response were photographed.

| Group | LipofectAMINE ™ (µl) | Polybrene ™ (µg/ml final) | FBS |
|---|---|---|---|
| A | 6 | — | — |
| B | 6 | — | + |
| C | 18 | 20 | + |

$4 \times 10^4$ COS-7 cells were plated in 24-well plates. The day after plating, cells were transfected with 0.4 µg pCMV beta-gal DNA using LipofectAMINE™ reagent. The transfection medium was composed of 0.8 ml DMEM with or without Polybrene™ and 5% FBS. The day following transfection, the cells were rinsed with PBS, fixed and stained with X-gal. Peak activity points from the dose-response were photographed.

| Group | LipofectAMINE™ (μl) | Polybrene™ (μg/ml final) | FBS |
|---|---|---|---|
| A | 5 | — | — |
| B | 8 | — | + |
| C | 12 | 80 | + |

The optimal conditions from dose responses of LipofectAMINE™ and Polybrene™ in transfections with or without 5% FBS are as follows: With BHK21 (1×10$^5$), 8 μl of LipofectAMINE™ was used in the absence of FBS and Polybrene™; 9 μl of LipofectAMINE™ was used in the presence of FBS and the absence of Polybrene™, and 15 μl of LipofectAMINE™ was used in the presence of both FBS and Polybrene™. Polybrene™ was used at 20 μg/ml. The level of transfection (number of stained cells) in the presence of serum and Polybrene™ was nearly equivalent to that seen in serum-free conditions, however more cells survived (less toxicity), so the percent transfected cells is not as high.

With the COS-7 cells (4×10$^4$), 5 μl of LipofectAMINE™ was used in the absence of FBS and Polybrene™; 5 μl of LipofectAMINE™ was used in the presence of FBS and the absence of Polybrene™, and 12 μl of LipofectAMINE™ was used in the presence of both FBS and Polybrene™. Polybrene™ was used at 80 μg/ml. These cells showed less toxicity in response to serum-free LipofectAMINE™ transfection. Once again, the number of stained cells in the presence of serum and Polybrene™ is nearly equivalent to that seen in the serum-free transfection.

Example 2

The activity of β-galactosidase expression was determined from dose-response transfection experiments as described in Example 1. 1×10$^5$ BHK-21 cells were plated per 35 mm well (6-well plate). The day after plating, cells were rinsed with DMEM and fed 0.8 ml of DMEM with or without polybrene™ and 5% FBS. The cells were transfected with 1 μg pCMV β-gal DNA and LipofectAMINE™ Reagent. The day after transfection, cells were rinsed with PBS, harvested and assayed for β-galactosidase activity. Peak activity points from the dose-response were graphed as shown in FIG. 1.

The results at optimal conditions are as follows: At optimal LipofectAMINE™ concentration in the presence of 5% FBS, BHK-21 and COS-7 transfections showed a 20–30-fold increase in total activity of β-galactosidase when Polybrene™ was present in the transfection medium. The amount of LipofectAMINE™ required for peak activity in serum and Polybrene™ was higher than that required in serum-free medium.

| Group | LipofectAMINE™ (μl) | Polybrene™ (μg/ml final) | FBS |
|---|---|---|---|
| A | 6 | — | — |
| B | 6 | — | + |
| C | 18 | 20 | + |

Figure 2:
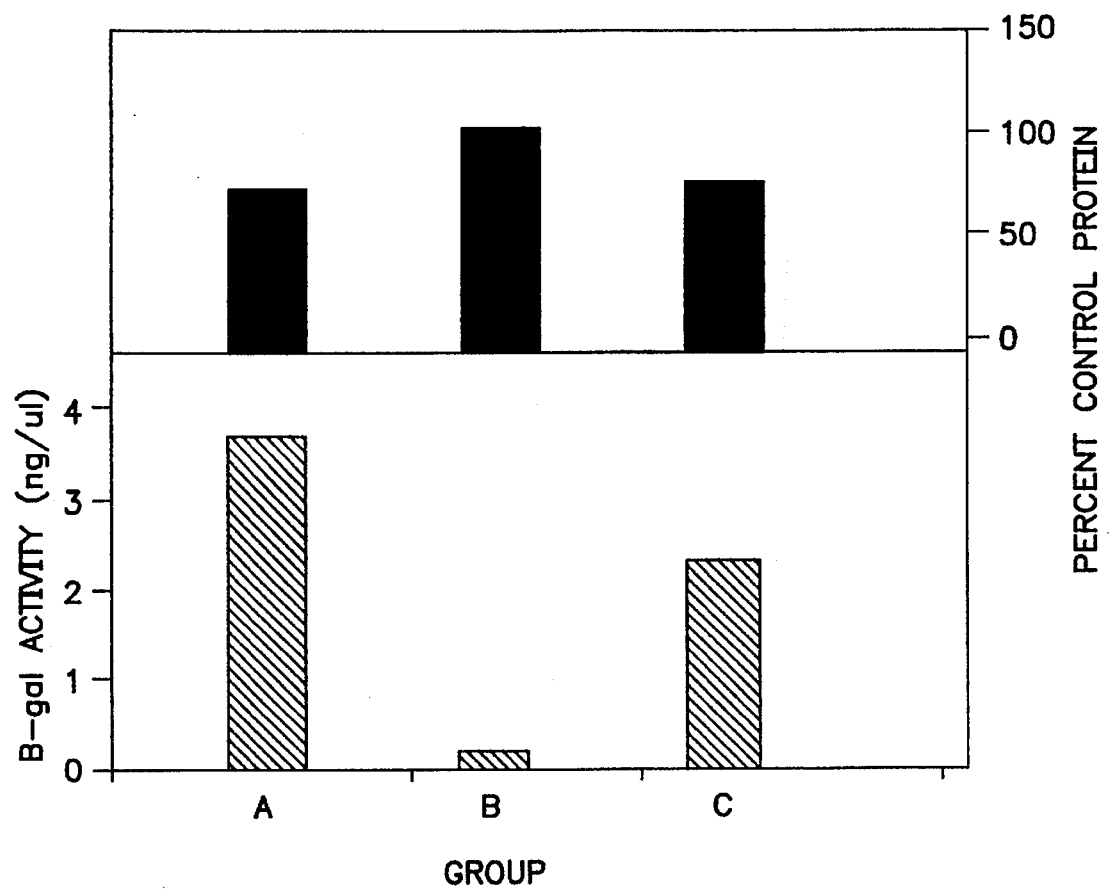
FIG. 2 is a bar graph showing Polybrene™ enhancement of β-gal activity in transfection of COS-7 Cells in serum and inhibition of protein levels in the presence of serum. Group A are cells transfected using 5 μl LipofectAMINE™, no Polybrene™ and no fetal bovine serum (FBS); Group B are cells transfected using 8 μl LipofectAMINE™, and no Polybrene™, with 5% fetal bovine serum present; Group C are cells transfected using 12 μl LipofectAMINE™, and 80 μl Polybrene™, with 5% fetal bovine serum present.

4×10$^4$ COS-7 cells were plated in 24-well plates. The day after plating, cells were transfected with 0.4 μg pCMV beta-gal DNA using LipofectAMINE™ reagent. The transfection medium was composed of 0.8 ml DMEM with or without Polybrene™ and 5% FBS. The day following transfection, the cells were rinsed with PBS, harvested and assayed for β-galactosidase activity. Peak activity points from the dose-response were graphed as shown in FIG. 2.

| Group | LipofectAMINE™ (μl) | Polybrene™ (μg/ml final) | FBS |
|---|---|---|---|
| A | 5 | — | — |
| B | 8 | — | + |
| C | 12 | 80 | + |

When LipofectAMINE™ is used in transfections in the presence of serum, activity is much lower than without serum, and the peak position for LipofectAMINE™ concentration shifts. When the serum-containing medium is supplemented with 20–40 μg per ml of Polybrene™, activity is greatly enhanced.

As will be appreciated by those skilled in the art, the foregoing examples are illustrative only and not meant to limit the scope of this invention which is defined by the appended claims and by equivalents to the claimed embodiments which would be obvious to one skilled in the art in view of the teachings herein.

We claim:

1. In a method of transfecting an animal cell in the presence of serum, comprising contacting said cell with a lipid aggregate comprising nucleic acid and a cationic lipid, wherein the improvement comprises: contacting said cell with said lipid aggregate in the presence of a polycationic compound, thereby transfecting said animal cell with said nucleic acid.

2. In a method of transfecting an animal cell in the presence of serum, comprising contacting said cell with a lipid aggregate comprising nucleic acid and a cationic lipid, wherein the improvement comprises: either (a) first contacting said cell with a polycationic compound to form a complex of said cell with said polycationic compound followed by contacting said cell complex with said lipid aggregate; or (b) first contacting said lipid aggregate with said polycation compound to form a mixture followed by contacting said cell with said mixture, thereby transfecting said animal cell with said nucleic acid.

3. A method of claim 2 wherein said polycationic compound is POLYBRENE™.

4. A method of claim 2 wherein said lipid aggregate comprises a compound toxic to said cells.

5. A method of claim 2 wherein said cells are mammalian cells.

6. A method of claim 2 wherein said serum is fetal bovine serum.

7. A method of claim 2 wherein said serum is human serum.

8. A method of claim 2 wherein said lipid aggregate comprises LipofectAMINE™.

9. A method of claim 2 wherein said lipid aggregate comprises Lipofectin™.

10. A method of claim 2 wherein said lipid aggregate comprises LipofectACE™.

11. A method of claim 2 wherein said nucleic acid is DNA.

* * * * *